(12) United States Patent
Warring-Davies

(10) Patent No.: US 7,338,453 B2
(45) Date of Patent: Mar. 4, 2008

(54) HAEMODYNAMIC MONITORING

(75) Inventor: Kenneth James Patrick Peter Warring-Davies, Bradford (GB)

(73) Assignee: Medics Limited, Bradford (GB)

( * ) Notice: Subject to any disclaimer, the term of this patent is extended or adjusted under 35 U.S.C. 154(b) by 271 days.

(21) Appl. No.: 10/495,411

(22) PCT Filed: Nov. 13, 2002

(86) PCT No.: PCT/GB02/05128

§ 371 (c)(1),
(2), (4) Date: Oct. 27, 2004

(87) PCT Pub. No.: WO03/041587

PCT Pub. Date: May 22, 2003

(65) Prior Publication Data

US 2005/0049511 A1 Mar. 3, 2005

(30) Foreign Application Priority Data

Nov. 13, 2001 (GB) ................................. 0127209.5

(51) Int. Cl.
*A61B 5/00* (2006.01)
(52) U.S. Cl. ...................................... 600/485; 600/500
(58) Field of Classification Search ..................... None
See application file for complete search history.

(56) References Cited

U.S. PATENT DOCUMENTS

| 5,103,828 | A | | 4/1992 | Sramek | 128/668 |
| 5,423,323 | A | * | 6/1995 | Orth | 600/486 |
| 5,584,298 | A | * | 12/1996 | Kabal | 600/485 |
| 5,788,647 | A | | 8/1998 | Eggers | 600/526 |
| 5,830,150 | A | | 11/1998 | Palmer et al. | 600/523 |
| 6,167,412 | A | * | 12/2000 | Simons | 708/105 |

FOREIGN PATENT DOCUMENTS

EP 0297675 A1 1/1989

OTHER PUBLICATIONS

Warring-Davies et al., "A New Technique for Monitoring Central Venous Pressures and Determining Cardiac Index in Adults," *Technology and Health Care*, 4: 233-238 (1996).
International Search Report issued Jul. 4, 2003 for corresponding PCT application No. PCT/GB02/05128.

* cited by examiner

*Primary Examiner*—Robert L. Nasser
(74) *Attorney, Agent, or Firm*—Myers Bigel Sibley & Sajovec

(57) ABSTRACT

Mean Pulmonary Arterial Pressure (MPAP), Mean Pulmonary Capillary Wedge Pressure (MPCWP) and Cardiac Index are all determinable (in a method or employing apparatus) from Central Venous Pressure (CVP), Mean Arterial Pressure (MAP), Heart Rate (HR), and Core Body Temperature (T) from the following relationships: MPAP=(a×MAP)+CVP (for MAP<58), or Va; MPAP=(a×MPAP)+CVP−(10×INT[(MAX {MAP−109), (CVP−7),0})/10]) for MAP>58); Vb; MPCWP=(b×MPAP)+CVP−(10×INT [CVP−7/10]; and VI; CI=K (T.CVP)/HR2, VII; where a and b are about 0.15; MAX (x, y, z)=largest of the three terms x, y, and z; INT [x]=integer part of x; MAP and CVP is measured in mmHg; T in Celsius and HR in counts per minute; CI is liters per square meter per minute; and K is a variable constant whose value is between 0 and 1000 depending on the values of CVP and HR.

16 Claims, 1 Drawing Sheet

HAEMODYNAMIC MONITORING

RELATED APPLICATIONS

The present application is a 35 U.S.C. §371 national phase application of PCT International Application No. PCT/GB02/05128, having an international filing date of Nov. 13, 2002, and claiming priority to Great Britain Patent Application No. 0127209.5, filed Nov. 13, 2001, the disclosures of which are incorporated herein by reference in their entireties. The above PCT International Application was published in the English language and has International Publication No. WO 03/041587 A2.

BACKGROUND OF THE INVENTION

The present invention relates to haemodynamic monitoring of human or animal patients. Baxter's Haemodynamic and Oxygenation Parameters lists a large number of body parameters which generally each have normal ranges of values for healthy patients. Departures from these values are useful tools for doctors treating patients to assist in diagnosis of the patient's condition, or for monitoring treatment or progress of a patient.

Such parameters are particularly valuable in intensive care situations, where they can give vital early warning signs that a patient needs attention.

Some of these parameters are very straightforward such as body temperature, mass and volume, heart rate, diastolic and systolic blood pressures, and even blood oxygen saturation. However, there are several which are more complicated and which require sophisticated monitoring systems.

The accompanying drawing is a schematic representation of the mammalian vascular system. The heart 10 has four chambers, the left and right atria ($L_A$, $R_A$) and the left and right ventricles ($L_V$, $R_V$). Each atrium supplies its respective ventricle. The right ventricle pumps blood to the lungs 12 through the pulmonary arteries 14.

Oxygenated blood is returned to the left atrium through the pulmonary veins 16. The left ventricle pumps blood into the aorta 18 which, through connecting arteries 19, supplies most parts of the body 20. Oxygen depleted blood returns through the veins 21 before arriving, finally, at the superior or inferior vena cava 22 which enters the right atrium.

Four basic blood pressures are of interest: Mean Pulmonary Artery Pressure (MPAP) (at 14); Mean Pulmonary Capillary Wedge Pressure (MPCWP or MPWP) also known as Mean Pulmonary Artery Occlusion Pressure (at 16); Central Venous Pressure (CVP) (at 22); and Mean Arterial Pressure (MAP) (at 14). Moreover the actual flow volume is also of significant interest (the cardiac index-CI), from which the Cardiac Output (CO) can be determined. CI is the blood flow per unit area of body surface (in square meters). Cardiac index, along with blood oxygen saturation levels, gives valuable information about a patient's condition, along with other parameters deducible from the foregoing, such as vascular resistance, stroke volume and work, etc.

Mean arterial blood pressure is the easiest to measure as this is what is measured when a person's blood pressure is normally taken. MAP is given by $$MAP = \frac{ASP + 2.ADP}{3} \qquad \text{I}$$

where ASP is the Arterial Systolic Pressure and ADP is the Arterial Diastolic Pressure. This formula assumes normal heart operation where, over each heart cycle, one-third is in systole and two-thirds is in diastole. The other three pressures are, however, difficult to measure and hitherto it has been done directly with quite a large degree of interpolation of results and some scepticism as to accuracy.

Currently, a catheter is available which comprises a flexible tube having an inflatable balloon at its tip, together with various pressure and temperature transducers. The catheter is inserted into a substantial vein 21 and fed back towards the heart. After insertion, the balloon is inflated so that it is carried by the blood flow and until it enters the right atrium, passes to the right ventricle and then into the pulmonary artery 16, where the balloon wedges in a first or second division of the pulmonary arteries.

When the balloon is deflated, the transducer measures directly Pulmonary Artery Pressure which, gives MPAP on the basis of a similar calculation to formula I above.

When the balloon is inflated, the pressure on the far side of the balloon from the heart is detected and taken as the MPCWP, or at least indicative thereof in a, hopefully, reproductive way. CVP is taken as an arbitrary proportion of MAP and other parameters, but otherwise is usually directly measured non-invasively, using a CVP catheter.

To measure Cardiac Output a thermo-dilution method is employed by injecting a set amount of a cold liquid into the catheter which exits the catheter upstream of the temperature transducer in the catheter. By monitoring the rise in temperature, the rate of fall, extrapolating the area under the graph, is indicative of the rate of blood flow.

A problem with this arrangement is that firstly it takes considerable skill to insert the catheter in the first place, not to mention the danger to the heart by insertion through it of the catheter. Secondly, there is no constant monitoring of three of the parameters mentioned above, namely MPAP, MPCWP and CI/CO, the first two being alternative measurements and the third being an average of at least three measurements within 10% of each other in a window of time. However, it is feasible that constant monitoring can be arranged but it requires more complication in the design of the catheter and constant known volume rate injection of the cold liquid. In any event, however, there are serious doubts as to the accuracy of measurements made and parameters calculated thereon. Physicians tend only to employ the results generated as a guide to, or confirmation of, diagnoses employing other methods, and the types of treatment that may be required.

An alternative means of measuring Cardiac Output employs a Doppler Oesophogeal probe; but that is only capable of determining Cardiac Output and Index.

Nevertheless, there is a need for a simpler and more reliable means of determining these essential haemodynamic parameters and it is an objective of the present invention to provide such a means.

BRIEF DESCRIPTION OF THE DRAWINGS

Other features of the present invention will be more readily understood from the following detailed description of specific embodiments thereof when read in conjunction with the accompanying drawings, in which.

DETAILED DESCRIPTION OF EMBODIMENTS

Figure 1:
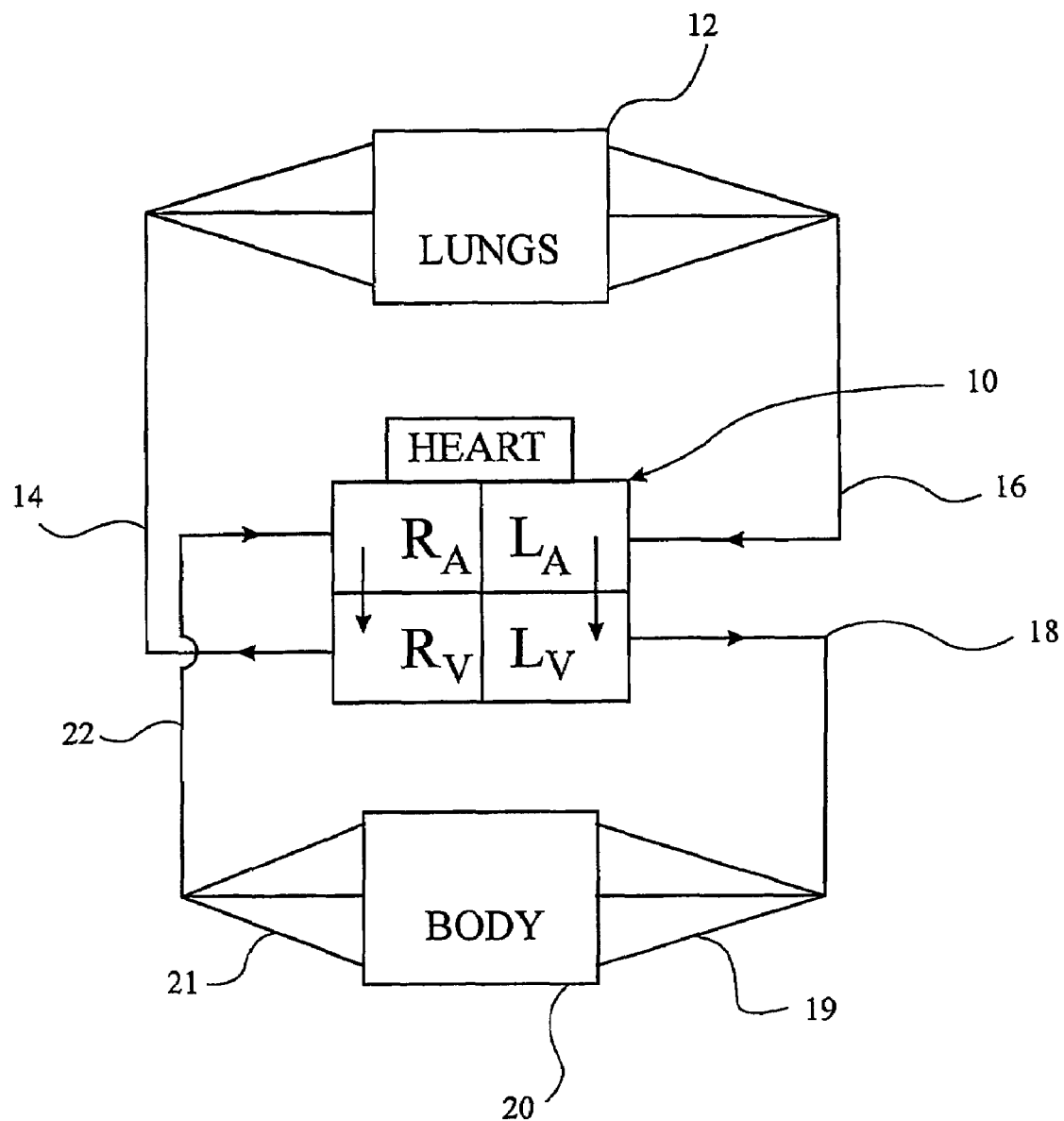
FIG. 1 is a schematic representation of the mammalian vascular system.

The present invention is based on two fundamental realisations. The first is well known: namely that blood flow in the four sectors of the heart must be the same. However, it has now been appreciated that this fact leads to the following relationships:

$$MPAP = f(MAP, CVP) \qquad \text{II}$$

$$MPCWP = f(MPAP, CVP) \qquad \text{III}$$

The second novel realisation is that blood flow rate appears to be a function of the square of the heart rate (in fact the inverse of the square of the heart rate). This leads to the following relationship:

$$CI = f(HR^2, CVP, T) \qquad \text{IV}$$

where HR is the heart rate and T is body core temperature.

Accordingly, the only parameters that need to be measured to enable determination of the essential haemodynamic parameters are MAP, HR, CVP and T, the remaining parameters MPAP, MPCWP and CI being determinable therefrom.

In accordance with a first aspect of the present invention, there is therefore provided a method of determining without direct measurement at least one of MPAP, MPCWP and CI by measuring or determining CVP and MAP and/or HR and T and employing one or more of the relationships:

$$MPAP = f(MAP, CVP);$$

$$MPCWP = f(MPAP, CVP); \text{ and}$$

$$CI = f(CVP, HR^2, T),$$

where MPAP, MPCWP, CL MAP, CVP, HR and T are as defined above.

In accordance with a different aspect of the present invention, there is provided apparatus for determining at least one of MPAP, MPCWP and CI comprising means to measure or determine CVP and MAP and/or HR and T and calculation means to resolve one or more of the relationships:

$$MPAP = f(MAP, CVP);$$

$$MPCWP = f(MPAP, CVP); \text{ and}$$

$$CI = f(CVP, HR^2, T),$$

where MPAP, MPCWP, CL MAP, CVP, HR and T are as defined above.

Examples of equations available within the relationships mentioned above are:

$$MPAP = (a_1 \times MAP) + CVP - k_1 \qquad \text{V}$$

$$MPCWP = (a_2 \times MPAP) + CVP - k_2 \qquad \text{VI}$$

$$CI = K \frac{T \cdot CVP}{HR^2} \qquad \text{VII}$$

where $a_1$ and $a_2$ are constants;

$k_1$ and $k_2$ are variable constants based on the values of CVP and MAP;

MAP and CVP is measured in mmHg; T in Celsius; and ER in counts per minute;

CI is liters per square meter per minute; and

K is a variable constant whose value is between 0 and 1000 depending on the values of CVP and HR.

Preferably, $a_1$ and $a_2$ are each separately between 0.01 and 1.0, more preferably between 0.10 and 0.25, and probably between 0.15 and 0.20.

Preferably, for MAP less than 58 mmHg:

$$k_1 = 0; \qquad \text{Va}$$

but for MAP equal to or greater than 58 mmHg:

$$k_1 = 10 \times \text{INT}[(\text{MAX}\{(MAP-109), (CVP-7), 0\})/10]) \qquad \text{Vb}$$

where MAX $\{[x, y, z]$ = largest of the three terms x, y and z; and

INT [x] = integer part of x. Preferably:

$$k_2 = 10 \times MNT [CVP-7/10] \qquad \text{VIa}$$

The best fit of the above formula VII is made when values of K are selected from Table 1 below

TABLE 1

| Values of HR in counts/min | Values of CVP in mmHg | | | | | | | |
|---|---|---|---|---|---|---|---|---|
| | 0-5 | 5-7 | 7-10 | 10-14 | 14-15 | 15-16 | 16-25 | >25 |
| 0-59 | 40 | 40 | 32 | 36 | 40 | 27.5 | 19.5 | 20 |
| 60-68 | 100 | 90 | 56 | 36 | 40 | 40 | 24 | 20 |
| 68-84 | 100 | 90 | 80 | 40 | 40 | 40 | 24 | 20 |
| 84-88 | 100 | 90 | 80 | 40 | 40 | 60 | 24 | 20 |
| 88-96 | 100 | 90 | 80 | 100 | 100 | 80 | 24 | 20 |
| 96-99 | 100 | 95 | 90 | 100 | 100 | 80 | 24 | 20 |
| >=100 | 100 | 100 | 100 | 100 | 100 | 80 | 60 | 50 |

Preferably said apparatus includes means to receive measured values of MAP, CVP, T and HR and outputs at least one, and preferably all, the parameters MPAP, MPCWP, and CI based on computations using formulae V, VI and VII above. Preferably K values employed are as set out in Table 1 above.

The formulae identified above have been distilled from the Map of Empirical Physiological Formulae for Determining Cardiac Index shown in Table 2 below and the Physiological Flowcharts for MPAP and MPCWP shown in Table 3 below. Both Tables 2 and 3 have been derived from physiological studies and investigations.

Preferably said apparatus further includes a Central Venous Pressure transducer catheter, which is capable of insertion in the body of a patient into a major vein and being directed to monitor pressure in or near a vessel entering the right atrium of the heart.

Such a procedure is much simpler than one involving passage through the heart and offers much less risk to the patient.

Indeed, along with the aforementioned parameters, Cardiac Output and many other useful parameters can now be determined from the relatively simply measured parameters of MAP, CVP, HR and T, as well as other conventional measurements such as body weight and height, oxygen saturation etc. For example, many of the parameters in Baxter's Haemodynamic and Oxygenation Parameters, such as Systemic, or Pulmonary, Vascular Resistance.

Referring to Table 2, this represents a map of formulae to be employed (depending on the values of CVP and HR measured) by which CI is calculated.

It is envisaged that a man skilled in the art of computing will have no difficulty in implementing apparatus which selects the appropriate formula depending on the values of CVP and HR measured and outputting Cardiac Index values. If height and weight is also input, then Cardiac Output (CO) can easily be calculated from the relationship.

$$CO = BSA \times CI \qquad \text{VIII}$$

where CO is in liters per minute and BSA is the body surface area in square metres. BSA can be determined from body weight (WT) and height (HT) and the empirical formula:

$$BSA = 0.17\sqrt{Ht.Wt} \qquad \text{IX}$$

where Ht is in metres and Wt is in kilograms.

Since there is overlap between some of the fields (which cater for different physiological conditions that might be expected in different circumstances) either the K value in one of the fields can be chosen, based on the experience of the physician, or a compromise figure for K may be employed. Indeed, that is what the values in Table 1 above represent where fields overlap. Moreover, given formula VII above, said apparatus may include a look-up table incorporating the values of K in Table 1 above, so that, on input of values for CVP and HR an appropriate value of K is selected and applied in formula VII above to calculate CI.

TABLE 2

Map of Empirical Physiological Formulae for Determining Cardiac Index using 'K' values

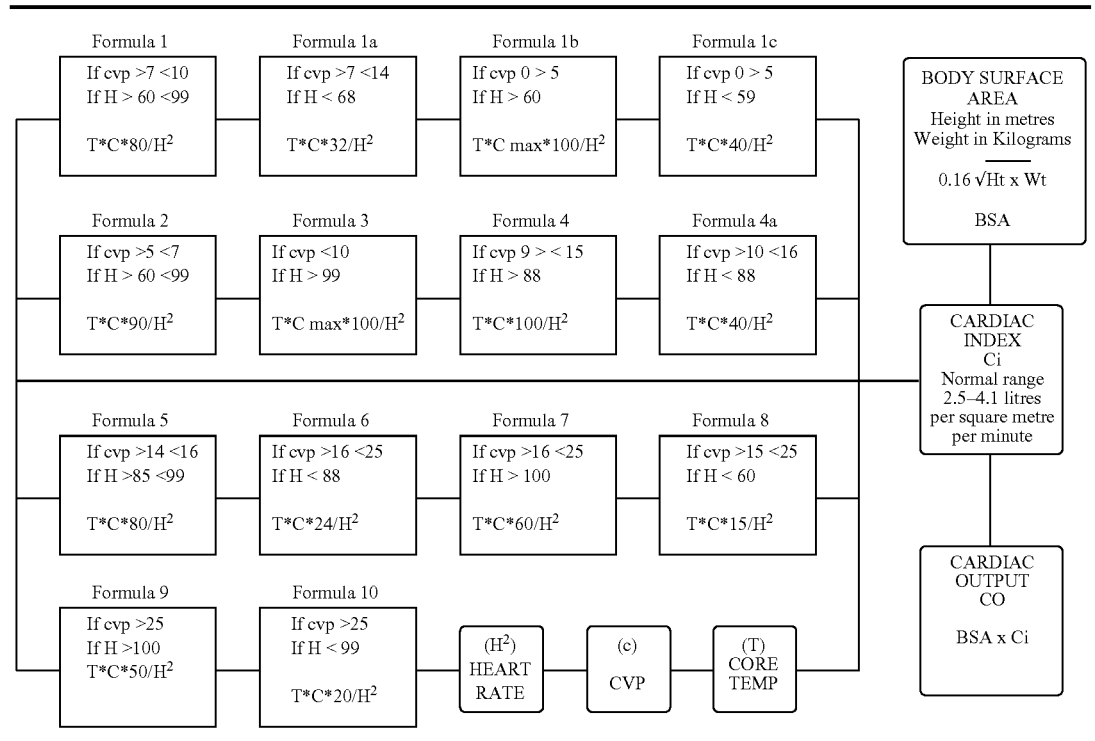

At demarkation points take best fit and divide by the number of subsets used

TABLE 3

Physiological Flowcharts for MPAP & MPWP

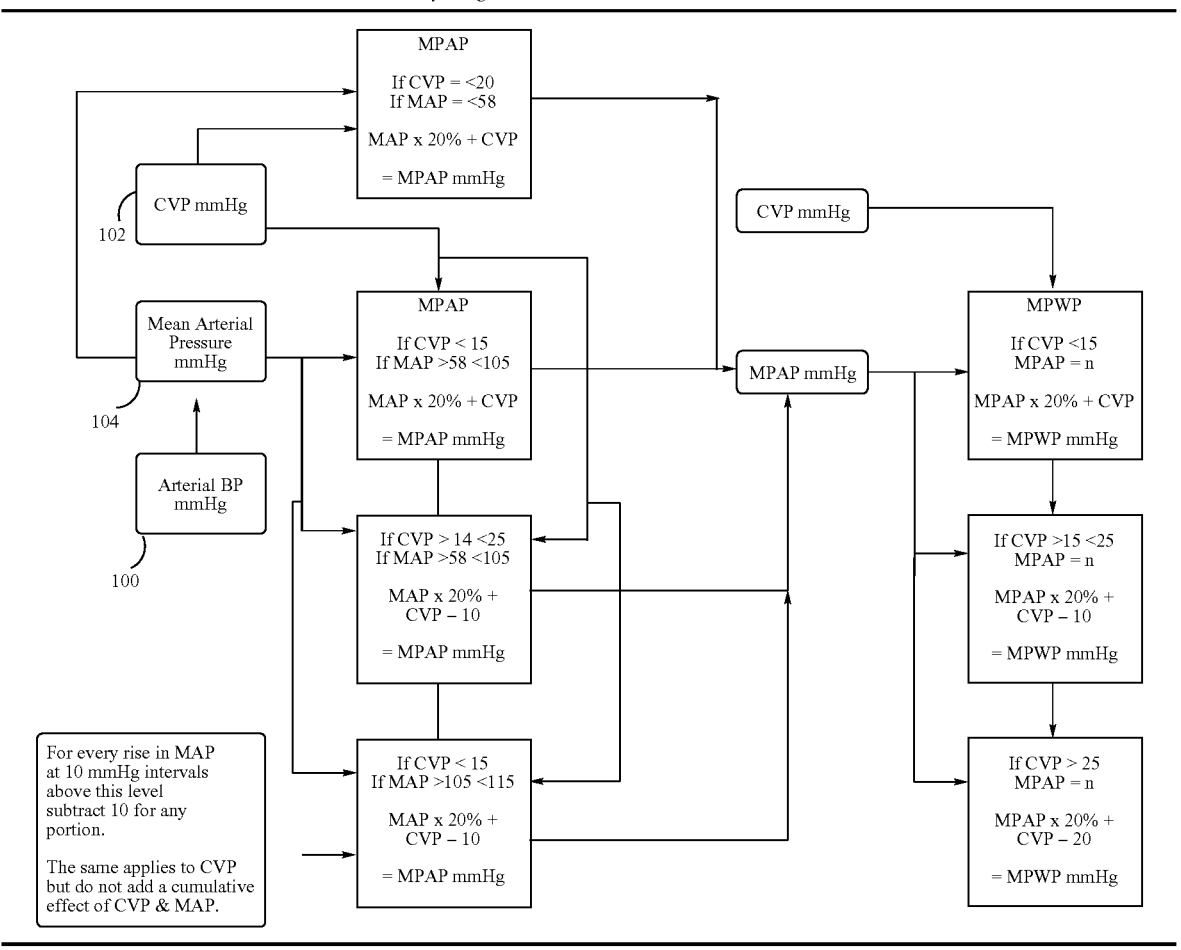

From this it is apparent that Table 1 could be either expanded in one or both directions, (ie employing smaller, and therefore more, ranges of values of CVP and HR) or it could be contracted. Clearly this is merely a question of refinement. Similarly, the absolute values of K given in the table are somewhat arbitrary and it is likely that adjustments may be made from time to time as the relationships between the various parameters become better understood under various circumstances.

Referring to Table 3, this flowchart is likewise easily executable in computing terms and is a representation of the formulae Va and b and VIa above.

The process begins with two inputs 100, 102, the first 100 being arterial blood pressures detected by any appropriate means and from which MAP 104 is immediately deducible. The second is CVP, measured preferably with a catheter as described above.

MPAP is essentially between 10% and 20% of MAP, plus CVVP, less a correction factor determined by the values of CVP and MAP.

Likewise. MPCWP (also known as MPWP as used in Table 3) is essentially between 10% and 20% of MPAP, plus CVP, less a correction factor determined by the value of CVP.

Both these processes can be reduced to the formulae Va and b, and VIa above. It is to be especially noted that increases in both MAP and CVP beyond normal limits result in reduced values of both MPAP and MPCWP, but not cumulatively if both MAP and CVP are above normal. However, the larger of the two variants is employed to calculate the reduction.

Moreover both the formulae Vb and VIa, and Table 3 suggest adjustment of the respective MPAP and MPCWP determinations on the basis of 10 mmHg increases in MAP and/or CVP. However, different arbitrary orders for adjustment could be employed indeed even a progressive adjustment, rather than the stepwise adjustment suggested here could be employed.

It should be borne in mind that the fundamental aspects of the present invention is the appreciation that helpfully representative approximations of the haemodynamic parameters referred to herein can be gained from generalised relationships set out in formulae II, m and IV of which the formulae V (a and b), VI (a) and VII or Tables 2 and 3, are current best approximations. Future studies may refine any of these formulae to provide more accurate values for MPAP, MPCWP and CI in particular circumstances.

Indeed, no attempt is made herein to explain why the relationships appear to hold true, since such theorisation has no bearing on the present invention.

Although invasive methods of measuring CVP are known, non-invasive methods can also be employed, such as by employing a surrogate of CVP, for example the jugular venous pressure. When a patient has a pulmonary constriction, CVP increases substantially so that a pressure pulse feeds back up the jugular vein where it can be detected on the surface of the neck. A simple measurement of the height of the pulse above the zero point of the atrium indicates CVP.

In this way, nearly all common haemodynamic parameters can be established for a patient without entering the body.

Furthermore, because the method employed by the present invention is truly continuous it can be employed to control treatment devices which are required to respond to haemodynamic parameters less invasively or non-invasively. An obvious application is to a heart pacemaker. A probe constantly monitoring CVP, T and HR inside the body can supply a processor which in turn determines appropriate haemodynamic parameters on the basis of the formulae described herein. Such parameters are then themselves employed to control the operation of the pacemaker.

Other potential applications include drug delivery systems, for example, and also the newly developing field of telemedicine. The following Table 4 shows five sets of measurements using both Pac (pulmonary artery catheter (Swan-Ganz)—a thermo-dilution method) and CCDM (the continuous cardiac dynamic monitoring formulae of the present invention) and gives the results of measurement on a patient who had been subject to open heart surgery and just been taken off an extracorporeal bypass machine.

All of the constants in each set of formulae, e.g. for deriving cardiac index, mean pulmonary arterial pressure and mean pulmonary wedge or occlusion pressures, may vary over a wide range, e.g., from −10 to 1000.

The invention claimed is:

1. A method of determining at least one of MPAP, MPCWP and CI, comprising:
    obtaining CVP and MAP and/or HR and T from a subject using at least one sensor; and
    employing one or more of the relationships:

$$MPAP = f(MAP, CVP); \qquad \text{II}$$

$$MPCWP = f(MPAP, CVP); \text{ and} \qquad \text{III}$$

$$CI = f(CVP, HR^2, T), \qquad \text{IV}$$

where MPAP is mean pulmonary artery pressure, MPCWP is mean pulmonary capillary wedge pressure, CI is cardiac index, MAP is mean arterial pressure, CYP is central venous pressure, HR is heart rate, and T is body core temperature.

2. A method as claimed in claim 1, in which said relationships II, III and/or IV respectively comprise:

$$MPAP = (a_1 \times MAP) + CVP - k_1 \qquad \text{V}$$

$$MPCWP = (a_2 \times MPAP) + CVP - k_2 \qquad \text{VI}$$

$$CI = K \frac{T \cdot CVP}{HR^2} \qquad \text{VII}$$

TABLE 4

| Measurement | CI Pac | CI ccdm | MPAP Pac | MPAP ccdm | MPWP pac | MPWP ccdm | ART sys | ART dys | CVP | HR |
|---|---|---|---|---|---|---|---|---|---|---|
| 1 | 2.4 | 2.4 | 25 | 28 | 12 | 13 | 100 | 52 | 14 | 95 |
| 2 | 2.5 | 2.3 | 23 | 28 | 12 | 16 | 100 | 53 | 14 | 98 |
| 3 | 3.11 | 2.3 | 22 | 29 | 12 | 20 | 103 | 54 | 14 | 94 |
| 4 | 3.27 | 2.3 | 23 | 29 | 12 | 20 | 104 | 54 | 12 | 94 |
| 5 | 3.88 | 2.2 | 22 | 28 | 12 | 19 | 106 | 54 | 14 | 94 |

In the Table the abbreviation CI and MPAP have the meanings indicated above. MPWP means Mean Pulmonary Wedge Pressure, ART sys means Arterial systolic pressure and ART dys means Arterial diastolic pressure. CVP means central venus pressure and HR means heart rate. The readings in Table 4 indicate that the method of the present invention provides results which are at least as consistent as those provided by the thermo dilution method. The measurements were repeated half an hour and two hours later and similar results were obtained indicating that the patient was in a stable condition.

Medical staff are particularly interested in following the haemodynamic trends rather than a series of isolated measurements, that is to say, to see if a regime of therapy is working effectively.

Finally, although the present invention is described herein with reference to the flow rates in the circulatory system of human patients, the invention has application to other organs such as the stomach, liver etc. Furthermore, equivalent formulae apply to other mammals and possibly other vertebrates. Accordingly, at least in respect of mammals, such formulae may assist in veterinary treatment.

All of the physiological parameters with which the invention is concerned, i.e., heart rate, central venous pressure, mean arterial pressure and body temperature, can vary from one physiological extreme to the other.

where
  $a_1$ and $a_2$ are constants between about 0.01 and about 1.0;
  $k_1$ and $k_2$ are variable constants based on the values of CVP and MAP;
  MAP and CVP is measured in mmHg; T in Celsius; and HR in counts per minute;
  CI is liters per square meter per minute; and
  K is a variable constant whose value is between about 10 and about 100 depending on the values of CVP and HR.

3. A method as claimed in claim 2, in which, for MAP less than 58 mmHg:

$$k_1 = 0; \qquad \text{Va}$$

and for MAP equal to or greater than 58 mmHg:

$$k_1 = 10 \times INT[(MAX\{(MAP-109),(CVP-7),0\})/10]) \qquad \text{Yb}$$

where
  MAX $\{x, y, z\}$ = largest of the three terms x, y and z;
  INT [x] = integer part of x.

4. A method as claimed in claim 2, in which:

$$k_2 = 10 \times INT \ [CVP-7/10]. \qquad \text{VIa}$$

5. A method as claimed in claim 2 in which K is selected from the following table:

TABLE 1

| Values of HR in counts/min. | Values of CVP in mmHg | | | | | | | |
|---|---|---|---|---|---|---|---|---|
| | 0-5 | 5-7 | 7-10 | 10-14 | 14-15 | 15-16 | 16-25 | >25 |
| 0-59 | 40 | 40 | 32 | 36 | 40 | 27.5 | 19.5 | 20 |
| 60-68 | 100 | 90 | 56 | 36 | 40 | 40 | 24 | 20 |
| 68-84 | 100 | 90 | 80 | 40 | 40 | 40 | 24 | 20 |
| 84-88 | 100 | 90 | 80 | 40 | 40 | 60 | 24 | 20 |
| 88-96 | 100 | 90 | 80 | 100 | 100 | 80 | 24 | 20 |
| 96-99 | 100 | 95 | 90 | 100 | 100 | 80 | 24 | 20 |
| >=100 | 100 | 100 | 100 | 100 | 100 | 80 | 60 | 50. |

6. Apparatus for determining at least one of MPAP, MPCWP and CI comprising:
sensor means to obtain CVP and MAP and/or HR and T; and
calculation means to resolve one or more of the relationships:

$$MPAP = f(MAP, CVP) \qquad \text{II}$$

$$MPCWP = f(MAP, CVP); \text{ and} \qquad \text{III}$$

$$CI = f(CVP, HR^2, T), \qquad \text{IV}$$

where MPAP is mean pulmonary artery pressure, MPCWP is mean pulmonary capillary wedge pressure, CI is cardiac index, MAP is mean arterial pressure, CVP is central venous pressure, HR is heart rate, and T is body core temperature.

7. Apparatus as claimed in claim 6, in which said relationships II, III and/or IV respectively comprise:

$$MPAP = (a_1 \times MAP) + CVP - k_1 \qquad \text{V}$$

$$MPCWP = (a_2 \times MPAP) + CVP - k_2 \qquad \text{VI}$$

$$CI = K \frac{T \cdot CVP}{HR^2} \qquad \text{VII}$$

where
$a_1$ and $a_2$ are constants between about 0.05 and about 0.3;
$k_1$ and $k_2$ are variable constants, preferably based on the values of CVP and MAP;
MAP and CVP is measured in mmHg; T in Celsius; and HR in counts per minute;
CI is liters per square meter per minute; and
K is a variable constant whose value is between about 0 and about 1000 depending on the values of CVP and HR.

8. Apparatus as claimed in claim 7, in which, for MAP less than 58 mmHg;

$$k_1 = 0 \qquad \text{Va}$$

and for MAP equal to or greater than 58 mmHg:

$$k_1 = 10 \times INT[(MAX\{(MAP-109), (CVP-7), 0\}) / 10]) \qquad \text{Vb}$$

where
MAX $\{x, y, z\}$ = largest of the three terms x, y and z;
TNT [x] = integer part of x.

9. Apparatus as claimed in claim 7, in which:

$$k_2 = 10 \times INT [CVP-7/10]$$

10. Apparatus as claimed in claim 7, in which K is selected from the following table:

TABLE I

| Values of HR in counts/mm | Values of CV? mmHg | | | | | | | |
|---|---|---|---|---|---|---|---|---|
| | 0-5 | 5-7 | 7-10 | 10-14 | 14-15 | 15-16 | 16-25 | >25 |
| 0-59 | 40 | 40 | 32 | 36 | 40 | 27.5 | 19.5 | 20 |
| 60-68 | 100 | 90 | 56 | 36 | 40 | 40 | 24 | 20 |
| 68-84 | 100 | 90 | 80 | 40 | 40 | 40 | 24 | 20 |
| 84-88 | 100 | 90 | 80 | 40 | 40 | 60 | 24 | 20 |
| 88-96 | 100 | 90 | 80 | 100 | 100 | 80 | 24 | 20 |
| 96-99 | 100 | 95 | 90 | 100 | 100 | 80 | 24 | 20 |
| >=100 | 100 | 100 | 100 | 100 | 100 | 80 | 60 | 50. |

11. Apparatus as claimed in claim 6, further comprising means to receive measured values of MAP, CVP, T and HR and means to output at least one of the parameters MPAP, MPCWP, and CI based on computations using said formulae.

12. Apparatus as claimed in claim 6, in which said relationship IV is derived from a Map of Empirical Physiological Formulae for Determining Cardiac Index.

13. Apparatus as claimed in claim 6, in which said relationship II and/or III is derived from Physiological Flowcharts for MPAP and MPCWP.

14. Apparatus as claimed claim 6, further comprising a Central Venous Pressure transducer catheter, which is capable of insertion in the body of a patient into a major vein and be directed to monitor CVP in or near a vessel entering the right atrium of the heart.

15. Apparatus as claimed in claim 6, further comprising display means to display values of MPAP, MPCWP and/or CI based on said measurements and formulae.

16. Apparatus as claimed in claim 15, further comprising means to calculate and display other haemodynamic parameters based on MAP, CVP, HR, T, MPAP, MPCWP, and/or CI.

* * * * *

UNITED STATES PATENT AND TRADEMARK OFFICE
CERTIFICATE OF CORRECTION

PATENT NO.        : 7,338,453 B2                                   Page 1 of 1
APPLICATION NO.   : 10/495411
DATED             : March 4, 2008
INVENTOR(S)       : Warring-Davies It is certified that error appears in the above-identified patent and that said Letters Patent is hereby corrected as shown below:

Column 10, Claim 1, Line 19:   Please correct "CYP" to read -- CVP --

Column 10, Claim 3, Line 58:   Please correct "Yb" to read -- Vb --

Signed and Sealed this

Fifth Day of August, 2008

JON W. DUDAS
*Director of the United States Patent and Trademark Office*